US005882671A

United States Patent [19]
Helton et al.

[11] Patent Number: 5,882,671
[45] Date of Patent: *Mar. 16, 1999

[54] ANXIOLYTIC AGENTS

[75] Inventors: David Reed Helton; Mary Jeanne Kallman, both of Greenfield; James Allen Monn; Darryle Darwin Schoepp, both of Indianapolis; Joseph Patrick Tizzano, New Palestine, all of Ind.

[73] Assignee: Eli Lilly and Company, Indianapolis, Ind.

[ * ] Notice: The term of this patent shall not extend beyond the expiration date of Pat. No. 5,661,184.

[21] Appl. No.: 786,170

[22] Filed: Jan. 21, 1997

Related U.S. Application Data

[63] Continuation-in-part of Ser. No. 496,710, Jun. 29, 1995, abandoned, which is a continuation-in-part of Ser. No. 337,349, Nov. 10, 1994, abandoned, which is a continuation-in-part of Ser. No. 289,957, Aug. 12, 1994, abandoned.

[51] Int. Cl.$^6$ ...................................................... A61K 9/64
[52] U.S. Cl. .......................... 424/456; 424/464; 424/451; 424/422; 514/574; 514/820; 514/811
[58] Field of Search ..................................... 424/422, 456, 424/464; 514/574, 810, 811, 812, 813

[56] References Cited

U.S. PATENT DOCUMENTS 5,661,184  8/1997  Helton ...................................... 514/574

FOREIGN PATENT DOCUMENTS

95/15940  6/1995  WIPO .

OTHER PUBLICATIONS

Y. Nakagawa et al., "(2S, 3S, 4S) α–(Carboxycyclopropyl)–glycine is a novel agonist of metabotropic glutamate receptors," *European J. Pharmacology*, 184, 205–206 (1990).

Y. Hayashi et al., "Agonist analysis of 2–(carboxy–cyclopropyl) glycine isomers for cloned metabotropic glutamate receptor subtypes expressed in Chinese hamster ovary cells," *Br. J. Pharmacol.*, 107, 539–543 (1992).

H. Shinozaki and M. Ishida, "Recent Advances in the Study of Glutamate Receptor Agonists," *Asia Pacific J. of Pharmacol.*, 6, 293–316 (1991).

F. Nicoletti et al., "($2_S$, $1'_R$, $2'_R$, $3'_R$)–2–(2,3–Dicarboxycyclopropyl) glycine enhances quisqualate–stimulated inositol phospholipid hydrolysis in hippocampal slices," *Eur. J. Pharmacol. –Molecular Pharmacol. Section*, 245, 297–298 (1993).

M. Ishida et al., "A potent metabotropic glutamate receptor agonist: electrophysiological actions of a conformationally restricted glutamate analogue in the rat spinal cord and Xenopus oocytes, " *Brain Res.*, 537, 311–314 (1990).

M. Ishida et al., "A novel metabotropic glutamate receptor agonist: marked depression of monosynaptic excitation in the newborn rat isolated spinal cord," *Br. J. Pharmacol.*, 109, 1169–1177 (1993).

V. Bruno et al., "Protective effect of the metabotropic glutamate receptor agonist, DCG–IV, against excitotoxic neuronal death," *Eur. J. Pharmacol.*, 256, 109–112, (1994).

H. Kaba et al., "Induction of an Olfactory Memory by the Activation of a Metabotropic Glutamate Receptor," *Science*, 265, 262–264 (Jul. 8, 1994).

D.E. Jane et al., "Actions of two new antagonists showing selectively for different sub–types of metabotropic glutamate receptor in the neonatal rat spinal cord," *Br. J. Pharmacol.*, 112, 809–816 (1994).

F. Nicoletti et al., "Effect of Metabotropic Glutamate Receptor Agonists on Excitotoxic or Apoptopic Neuronal Degeneration," *Neuropschychopharmacology*, 10 (3S), 623S (1994).

M. Koch, "Microinjections of the metabotropic glutamate receptor agonists, trans–(+)–1–amino–cyclopentane–1,3–dicarboxylate (trans–ACPD) into the amygdala increase the acoustic startle response of rats," *Brain Research*, 629, 176–179 (1993).

D. Schoepp and B. Johnson, "Metabotropic Glutamate Receptor Modulation of cAMP Accumulation in the Neonatal Rat Hippocampus," *Neuropharmacology*, 32(12), 1359–1365 (1993).

Davis, TiPS, 13, 35–41 (Jan., 1992).

*Primary Examiner*—Thurman K. Page
*Assistant Examiner*—D. Faulkner
*Attorney, Agent, or Firm*—Martin A. Hay; David E. Boone

[57] ABSTRACT

The present invention provides a method of treating anxiety and related disorders using an agonist which acts at negatively coupled cAMP-linked metabotropic glutamate receptors.

6 Claims, No Drawings

ANXIOLYTIC AGENTS

This application is a continuation-in-part of application Ser. No. 08/496,710, filed Jun. 29, 1995, now abandoned, which is a continuation-in-part of application Ser. No. 08/337,349, filed Nov. 10, 1994 (now abandoned) which is itself a continuation-in-part of application Ser. No. 08/289,957 filed Aug. 12, 1994 (now abandoned).

BACKGROUND OF THE INVENTION

The present invention relates to the treatment of anxiety and related disorders.

The fourth edition of the Diagnostic and Statistical Manual of Mental Disorders (DSM-IV™), published in 1994 by the American Psychiatric Association, Washington, D.C., defines anxiety and related disorders. These are panic disorder without agoraphobia, panic disorder with agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified.

Anxiety disorders are generally treated by counseling or with drugs. Classes of drugs which are widely prescribed for the treatment of anxiety disorders include the benzodiazepines (such as diazepam) and buspirone hydrochloride.

The benzodiazepines were introduced during the 1960's. They have achieved widespread acceptance, but their use is nevertheless restricted due to their adverse side-effect profile, in particular their tendency to induce dependence.

Buspirone hydrochloride was introduced during the early 1980's. It lacks the dependence-inducing side effects of the benzodiazepines, but has a slow onset of action (about 4 weeks).

There is therefore a need for new drugs for the treatment of anxiety and related disorders.

Several animal models have been developed which are recognized in the art as being predictive of anxiolytic activity. These include the fear potentiated startle model, described by Davis in Psychopharmacology 62:1; 1979, Behav. Neurosci. 100:814;1986 and TiPS, January 1992 [Vol. 13] 35–41, the elevated plus model described by Lister in Psychopharmacol. 92:180–185;1987, and the well-known punished—responding (conflict) model, described, for example, in "Psychopharmacology of Anxiolytics and Antidepressants", edited by S. E. File, pp. 131–153, Raven Press, New York, 1991.

In the mammalian central nervous system (CNS), the transmission of nerve impulses is controlled by the interaction between a neurotransmitter, that is released by a sending neuron, and a surface receptor on a receiving neuron, causing excitation of this receiving neuron. The benzodiazepines and buspirone hydrochloride are both believed to exert their anxiolytic effect through binding to such receptors. In particular, the benzodiazepines are believed to act by binding to GABA receptors, while buspirone hydrochloride is believed to bind to $5HT_{1a}$ receptors.

L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, emotional states and sensory perception.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in cAMP formation, and changes in ion channel function. Schoepp and Conn, *Trends in Pharmacol. Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

The metabotropic glutamate receptors are a highly heterogeneous family of glutamate receptors that are linked to multiple second-messenger pathways. Generally, these receptors function to modulate the presynaptic release of glutamate, and the postsynaptic sensitivity of the neuronal cell to glutamate excitation. The metabotropic glutamate receptors (mGluR) have been pharmacologically divided into two subtypes. One group of receptors is positively coupled to phospholipase C, which causes hydrolysis of cellular phosphoinositides (PI). This first group are termed PI-linked metabotropic glutamate receptors. The second group of receptors is negatively coupled to adenyl cyclase, which prevents the forskolin-stimulated accumulation of cyclic adenosine monophosphate (cAMP). Schoepp and Conn, *Trends Pharmacol. Sci.*, 14, 13 (1993). Receptors within this second group are termed cAMP-linked metabotropic glutamate receptors.

It has now been found that a compound which is an agonist that acts selectively at negatively coupled cAMP-linked metabotropic glutamate receptors is effective in the fear potentiated startle and elevated plus maze models of anxiety (but does not have benzodiazepine-like efficacy in the punished-responding (conflict) model).

SUMMARY OF THE INVENTION

The present invention provides a method of treatment of anxiety and related disorders, which comprises administering to a mammal in need of treatment an effective amount of an agonist which acts at negatively coupled cAMP-linked metabotropic glutamate receptors.

DETAILED DESCRIPTION OF THE INVENTION

It has been found that a compound which acts selectively as an agonist at negatively coupled cAMP-linked metabotropic glutamate receptors, (+)-2-aminobicyclo[3.1.0]- hexane-2,6-dicarboxylic acid is effective in the fear potentiated startle and elevated plus maze models of anxiety. It has also been found that three other compounds which act selectively as agonists at negatively coupled cAMP-linked metabotropic glutamate receptors, namely 1SR,4SR,5RS, 6SR-4-amino-2-oxabicyclo[3.1.0]hexane-4,6-dicarboxylic acid; 1R,4R,5S,6R-4-amino-2-oxabicyclo[3.1.0]hexane-4,6-dicarboxylic acid and 1SR,4SR,5RS,6SR-4-amino-2-thiabicyclo[3.1.0]hexane-4,6-dicarboxylic acid are effective in the fear potentiated startle model. Since the benzodiazepines and buspirone hydrochloride are effective in these models and are useful generally in the treatment of anxiety disorders, it is believed that anxiety disorders will be treatable using any agonist which acts at negatively coupled cAMP-linked metabotropic glutamate receptors, especially an agonist which acts selectively.

The fear potentiated startle and elevated plus models both measure the ability of a test compound to protect a test animal from the effect of exposure to an anxiety-producing environment. In the former test, the anxiety-producing environment comprises a neutral stimulus, such as a light, which the test animal has been conditioned to associate with an adverse stimulus, such as an electric shock. In the latter test, the anxiety-producing environment comprises an open space, for which rodents have a natural aversion.

According to a preferred aspect, therefore, the present invention provides a method of protecting a mammal from the effect of an anxiety-producing environment, which comprises administering an effective amount of an agonist which acts at negatively coupled cAMP-linked metabotropic glutamate receptors, preferably an agonist which acts selectively.

It will be appreciated that the effect of an anxiety producing environment on a mammal may be conditioned (as measured in the fear potentiated startle model) or natural (as measured in the elevated plus maze model). Accordingly, a particular environment may produce anxiety in only specific individuals or in a general population.

Examples of anxiety disorders which can be produced in specific individuals are those described in the Diagnostic and Statistical Manual of Mental Disorders, published in 1994 by the American Psychiatric Association, Washington, D.C.

The particular dose of agonist administered according to this invention will of course be determined by the particular circumstances surrounding the case, including the activity of the particular agonist administered, the route of administration, the particular condition being treated, and similar considerations. The agonist can be administered by a variety of routes including oral, rectal, transdermal, subcutaneous, intravenous, intramuscular, or intranasal routes. Alternatively, the agonist may be administered by continuous infusion. A typical daily dose will contain from about 0.001 mg/kg to about 100 mg/kg of the agonist. Preferably, daily doses will be about 0.05 mg/kg to about 50 mg/kg, more preferably from about 0.1 mg/kg to about 20 mg/kg.

As described previously herein, it is preferred to use an agonist which acts selectively at negatively coupled cAMP-linked metabotropic glutamate receptors (relative to other glutamate receptors) in the methods according to the invention. Such an agonist may be a single compound, for example one of the four compounds named hereinabove, or two or more compounds which, in combination function as an agonist which acts selectively at negatively coupled cAMP-linked metabotropic glutamate receptors. Thus, there are compounds which act non-selectively at negatively coupled cAMP-linked metabotropic glutamate receptors, for example 1S,3R-1-aminocyclopentane-1,3-dicarboxylic acid (1S,3R-ACPD, the active isomer of trans-ACPD), which also acts at PI-linked metabotropic glutamate receptors (Schoepp and Johnson, Neuropharmacology Vol. 32, No. 12, 993, pages 1359–1365).

Agonists which act at negatively coupled cAMP-linked metabotropic glutamate receptors may be identified using the following experiment. Firstly, the affinity of a test compound for metabotropic glutamate receptors may be demonstrated by the selective displacement of (1S,3R)-1-aminocyclopentane-1,3-dicarboxylic acid-sensitive [$^3$H] glutamate binding to rat brain cell membranes. The binding of [$^3$H]glutamate ([$^3$H]Glu) is conducted with crude membranes of rat forebrain as described by Schoepp and True. Schoepp and True, Neuroscience Lett., 145, 100–104 (1992); Wright, McDonald, and Schoepp, J. Neurochem., 63, 938–945 (1994). The affinity of a test compound for the receptor may be expressed as the concentration of the test compound that inhibits 50% binding ($IC_{50}$), or the percent displacement of [$^3$H]Glu at a 10 µM or 100 µM concentration of the formula I compound. In this text, the $IC_{50}$ for (+)-2-aminobicyclo[3.1.0]hexane-2,6-dicarboxylic acid was found to be 0.18 µM.

The ability of a test compound to act as an agonist at negatively coupled cAMP-linked metabotropic receptors may be measured using the following method. Test compounds are tested for their ability to decrease forskolin-stimulated cAMP formation in the rat hippocampus and the rat cerebral cortex, using the procedures described in Schoepp and Johnson. Schoepp and Johnson, Neurochem. Int., 22, 277–283 (1993). In this test, (+)-2-aminobicyclo [3.1.0]hexane-2,6-dicarboxylic acid was found to give the result shown in Table II below.

TABLE II

| Inhibition of Forskolin-Stimulated cAMP Formation | |
|---|---|
| | $EC_{50}$ (µM) |
| Rat cerebral cortex | .055 ± .017 |
| Rat hippocampus | .036 ± .015 |

The ability of test compounds to treat anxiety or a related disorder may be demonstrated using the well known fear potentiated startle and elevated plus maze models of anxiety.

In the fear potentiated startle model, animals are exposed to a neutral stimulus such as light (conditioned stimulus) with an aversive stimulus such as a shock (unconditioned stimulus). Following conditioning, when the animals are presented with a loud acoustic stimulus, larger startle responses are elicited when the startle stimulus is preceded by light. The difference in amplitude between the startle response when conditioned animals are exposed to the aversive stimulus paired with a neutral stimulus and the startle response when the conditioned animal is exposed only to the aversive stimulus is known as fear potentiated startle. The amplitude of the startle response when the animal is exposed only to the aversive stimulus is known as the baseline startle. Test compounds which are effective in this model decrease the fear potentiated startle response. It is emphasized that what is being determined experimentally is the difference between the startle response with paired stimuli and the baseline startle; test compounds which are anxiolytics may increase, decrease or leave unchanged the baseline startle response. (Davis, TiPS, January 1992 [Vol. 13], 35–41).

The elevated plus maze model is based upon the natural aversion of rodents to height and open spaces.

Diazepam and buspirone hydrochloride, which are clinically proven anxiolytics, are effective at reducing the fear (increased startle response) associated with the presentation of light in the fear potentiated startle model, and in reducing the fear of open spaces in the elevated plus maze model.

Male Long Evans rats (180–400 g) or male NIH Swiss mice (18–35 g) were obtained from Harlan Sprague-Dawley, Cumberland, Ind., U.S.A. and acclimated at least 3 days before testing. Animals were housed at 23°±2° C. (relative humidity 30% to 70%) and given Purina Certified Rodent Chow and water ad libitum. The photoperiod was 12 hours of light and 12 hours of dark, with dark onset at approximately 1800 hours.

Test compounds were dissolved in a vehicle of purified water and neutralized with 5N NaOH to a pH of 7–8 when applicable. Diazepam (Sigma Chemical Company, St. Louis, Mo.) was suspended in purified water by the dropwise addition of Tween 80. Control animals received the respective vehicle.

Fear Potentiated Startle

SL-LAB (San Diego Instruments, San Diego, Calif.) chambers were used for conditioning sessions and for the production and recording of startle responses. A classical conditioning procedure was used to produce potentiation of startle responses. Briefly, on the first 2 days, rats were placed into dark startle chambers in which shock grids were installed. Following a 5-minute acclimation period, each rat received a 1 mA electric shock (500 ms) preceded by a 5 second presentation of light (15 watt) which remained on for the duration of the shock. Ten presentations of the light and shock were given in each conditioning session, rats were gavaged with a solution of test compound of water and startle testing sessions were conducted. A block of 10 consecutive presentations of acoustic startle stimuli (110 dB, non-light-paired) were presented at the beginning of the session in order to minimize the influences of the initial rapid phase of habituation to the stimulus. This was followed by 20 alternating trials of the noise alone or noise preceded by the light. Excluding the initial trial block, startle response amplitudes for each trial type (noise-alone vs. light+noise) were averaged for each rat across the entire test session. Data are presented as the difference between noise-alone and light+noise. (+)-2-Aminobicyclo[3.1.0]hexane-2,6-dicarboxylic acid was found to give an $ED_{50}$ of 0.3 mg/kg, p.o. in this test.

Automated Elevated Plus Maze

Construction of the elevated plus-maze was based on a design validated for mice by Lister (1987). The entire maze was made of clear Plexiglas. The maze was comprised of two open arms (30×5×0.25 cm) and two enclosed arms (30×5×15 cm). The floor of each maze arm was corrugated to provide texture. The arms extended from a central platform and angled at 90 degrees from each other. The maze was elevated to a height of 45 cm above the floor and illuminated by red light. Individual infrared photocells were mounted along each arm of the maze to monitor closed, open, or nosepoke activity. Mice were individually placed on the central platform of the maze and the number of closed arm, open arm, and nosepoke (poking head only into open arm from closed arm of maze) counts were recorded and used as a measure of arm entries and time spent on various sections of the maze over a five-minute test period.

Oral administration of (+)-2-aminobicyclo[3.1.0]hexane-2,6-dicarboxylic acid produced significant increases in open arm activity at doses of 1, 3 and 10 mg/kg. Nosepoke counts showed a significant increase at 3 mg/kg. Closed arm activity counts were not significantly altered at any dose of the compound.

(+)-2-Aminobicyclo[3.1.0]hexane-2,6-dicarboxylic acid may be prepared by reacting carbethoxymethyl dimethylsulfonium bromide with 2-cyclopenten-1-one in the presence of a base, such as 1,8-diazabicyclo[5.4.0]undec-7-ene to afford ethyl 2-oxobicyclo[3.1.0]hexane-6-carboxylate. This ester may then be reacted with an aqueous solution of potassium cyanide or sodium cyanide and ammonium carbonate to produce an intermediate hydantoin, (the Bucherer-Bergs reaction), which is then hydrolysed using sodium hydroxide, to afford a diastereomeric mixture of diethyl 2-aminobicyclo[3.1.0]hexane-2,6-dicarboxylates. The desired diastereomer may be obtained by crystallization with oxalic acid. This diastereomer may then be resolved by forming a crystalline salt with (+)-di-p-toluoyl-D-tartaric acid and recovering (−)-diethyl 2-aminobicyclo[3.1.0]hexane-2,6-dicarboxylate. Hydrolysis of this diester using aqueous sodium hydroxide gives (+)-2-aminobicyclo[3.1.0]hexane-2,6-dicarboxylic acid. Alternatively, the ethyl 2-oxobicyclo[3.1.0]hexane-6-carboxylic acid may be hydrolysed using sodium hydroxide to give 2-oxobicyclo[3.1.0]hexane-6-carboxylic acid. This acid may then be resolved by forming a crystalline salt with (S)-1-phenylethylamine and recovering (+)-2-oxobicyclo[3.1.0]hexane-6-carboxylic acid. This acid may then be converted into (+)-2-aminobicyclo[3.1.0]hexane-2,6-dicarboxylic acid by reaction with an aqueous solution of potassium cyanide or sodium cyanide and ammonium carbonate to produce an intermediate hydantoin (the Bucherer-Bergs reaction) followed by hydrolysis of the hydantoin using sodium hydroxide. This procedure may also be modified by performing the resolution step on the hydantoin rather than on the 2-oxobicyclo[3.1.0]hexane-6-carboxylic acid. In this case, (R)-1-phenylethylamine has been found to be a suitable resolving agent.

The agonists are preferably formulated prior to administration in combination with one or more pharmaceutically-acceptable carriers, diluents, or excipients. The pharmaceutical formulations are prepared by known procedures using well-known and readily available ingredients. In making the compositions, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, dermal patch, subcutaneous implant, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, stearic acid, and mineral oil. The formulations can additionally include lubricating agents, wetting agents (surfactants), emulsifying and suspending agents, preserving agents, sweetening agents, or flavoring agents. Compositions may be formulated so as to provide quick, sustained, or delayed release of the active ingredient after administration to the patient by employing procedures well known in the art.

The compositions are preferably formulated in a unit dosage form, each dosage containing from about 1 mg to about 500 mg, more preferably about 5 mg to about 200 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1

Hard gelatin capsules are prepared using the following ingredients:

|  | Quantity (mg/capsule) |
|---|---|
| 2-Aminobicyclo[3.1.0]hexane-2,6-dicarboxylic Acid | 250 |
| Starch, dried | 200 |
| Magnesium stearate | 10 |
| Total | 460 mg |

The above ingredients are mixed and filled into hard gelatin capsules in 460 mg quantities.

Formulation 2

A tablet is prepared using the ingredients below:

|  | Quantity (mg/tablet) |
|---|---|
| 2-Aminobicyclo[3.1.0]hexane-2,6-dicarboxylic Acid | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight % |
|---|---|
| 2-Aminobicyclo[3.1.0]hexane-2,6-dicarboxylic Acid | 0.25 |
| Ethanol | 29.75 |
| Propellant 22 (chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

| 2-Aminobicyclo[3.1.0]hexane-2,6-dicarboxylic Acid | 60 mg |
|---|---|
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5

Capsules each containing 80 mg of active ingredient are made as follows:

| 2-Aminobicyclo[3.1.0]hexane-2,6-dicarboxylic Acid | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6

Suppositories each containing 225 mg of active ingredient may be made as follows:

| 2-Aminobicyclo[3.1.0]hexane-2,6-dicarboxylic Acid | 225 mg |
|---|---|

-continued

| Saturated fatty acid glycerides | 2,000 mg |
|---|---|
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of active ingredient per 5 ml dose are made as follows:

| 2-Aminobicyclo[3.1.0]hexane-2,6-dicarboxylic Acid | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation may be prepared as follows:

| 2-Aminobicyclo[3.1.0]hexane-2,6-dicarboxylic Acid | 100 mg |
|---|---|
| Mannitol | 100 mg |
| 5 N Sodium hydroxide | 200 ml |
| Purified water to total | 5 ml |

The following Examples further illustrate methods or their synthesis of (+)-2-aminobicyclo[3.1.0]hexane- 2,6-dicarboxylic acid. The Examples are not intended to be limiting to the scope of the invention in any respect, and should not be so construed. All experiments were run under a positive pressure of dry nitrogen or argon. All solvents and reagents were purchased from commercial sources and used as received, unless otherwise indicated. Dry tetrahydrofuran (THF) was obtained by distillation from sodium or sodium benzophenone ketyl prior to use. Proton nuclear magnetic resonance ($^1$H NMR) spectra were obtained on a GE QE-300 spectrometer at 300.15 MHz, a Bruker AM-500 spectrometer at 500 MHz, or a Bruker AC-200P spectrometer at 200 MHz. Free atom bombardment mass spectroscopy (FABMS) was performed on a VG ZAB-2SE instrument. Field desorption mass spectroscopy (FDMS) was performed using either a VG 70SE or a Varian MAT 731 instrument. Optical rotations were measured with a Perkin-Elmer 241 polarimeter. Chromatographic separation on a Waters Prep 500 LC was generally carried out using a linear gradient of the solvents indicated in the text. The reactions were generally monitored for completion using thin layer chromatography (TLC). Thin layer chromatography was performed using E. Merck Kieselgel 60 $F_{254}$ plates, 5 cm×10 cm, 0.25 mm thickness. Spots were detected using a combination of UV and chemical detection (plates dipped in a ceric ammonium molybdate solution [75 g of ammonium molybdate and 4 g of cerium (IV) sulfate in 500 mL of 10% aqueous sulfuric acid] and then heated on a hot plate). Flash chromatography was performed as described by Still, et al. Still, Kahn, and Mitra, *J. Org. Chem.*, 43, 2923 (1978). Elemental analyses for carbon, hydrogen, and nitrogen were determined on a Control Equipment Corporation 440 Elemental Analyzer, or were performed by the Universidad Complutense Analytical Centre (Facultad de Farmacia, Madrid, Spain). Melting points were determined in open glass capillaries on a Gallenkamp hot air bath melting point apparatus or a Buchi melting point apparatus, and are uncorrected. The number in parenthesis after the compound name refers to the compound number.

Preparation 1

Carbethoxymethyl Dimethylsulfonium Bromide

A solution of ethyl bromoacetate (265 g) and dimethyl sulfide (114 g) in acetone (500 mL) was stirred at room temperature. After three days, the title compound was isolated by filtration of the reaction mixture. Melting point 88°–90° C.

EXAMPLE 1

(1SR,5RS,6SR)Ethyl 2-Oxobicyclo[3.1.0]hexane-6-carboxylate

A suspension of carbethoxymethyl diethylsulfonium bromide (45.5 g) in toluene (350 mL) was treated with 1,8-diazabicyclo[5.4.0]undec-7-ene (30.2 g). The resulting mixture was stirred at room temperature. After one hour, the reaction mixture was treated with 2-cyclopenten-1-one (19.57 g). After an additional 18 hours, the reaction mixture was added to a 1N hydrochloric acid/sodium chloride solution. The resulting mixture was extracted with diethyl ether. The combined ether extracts were dried over magnesium sulfate, filtered, and concentrated in vacuo. The residue was purified using silica-gel chromatography, eluting with a linear gradient of 10% ethyl acetate/hexanes to 50% ethyl acetate/hexanes, to give 22.81 g of the title compound. Melting point: 36°–38° C.

FDMS: m/z=168 (M+).

Analysis calculated for $C_9H_{12}O_3$: C, 64.27; H, 7.19. Found: C, 64.54; H, 7.11.

EXAMPLE 2

(1SR,2RS,5RS,6SR)Diethyl 2-Aminobicyclo[3.1.0] hexane-2,6-dicarboxylate and (1SR,2SR,5RS,6SR)Diethyl 2-Aminobicyclo[3.1.0] hexane-2,6-dicarboxylate A solution of the compound prepared as described in Example 1 (22.81 g) in ethanol (200 mL) was treated with an aqueous solution of potassium cyanide (9.71 g) and ammonium carbonate (21.2 g) in water (200 mL). The resulting mixture was heated to about 50° C. After about 18 hours, the reaction mixture was allowed to cool to room temperature and treated with sodium hydroxide (16.2 g). The resulting mixture was heated to reflux. After about 18 hours, the reaction mixture was allowed to cool to room temperature, then cooled to 0° C. The pH of the cold mixture was adjusted to pH 1 by the addition of concentrated hydrochloric acid. This mixture was concentrated to dryness in vacuo. The residue was dissolved in ethanol, cooled to 0° C., and treated with thionyl chloride (80.6 g). The resulting mixture was heated to reflux. After about 48 hours, the reaction was concentrated to dryness in vacuo. The residue was treated with 1N sodium hydroxide, and the resulting mixture extracted with diethyl ether. The combined ether extracts were dried over potassium carbonate, filtered, and concentrated in vacuo to give 24.6 g of a mixture of the title compounds.

EXAMPLE 3

(1SR,2SR,5RS,6SR)Diethyl 2-Aminobicyclo[3.1.0] hexane-2,6-dicarboxylate

A solution of the compounds prepared as described in Example 2 (20.71 g) in ethyl acetate (200 mL) was treated with a solution of oxalic acid (15.46 g) in ethanol (50 mL). The resulting mixture was stirred at room temperature. After one hour, the reaction mixture was treated with additional ethanol (50 mL). After 18 hours, the mixture was filtered, and the filtrate was evaporated to dryness in vacuo. The residue was treated with 1N sodium hydroxide, and the resulting mixture extracted with diethyl ether. The combined ether extracts were washed with brine, dried over potassium carbonate, filtered, and concentrated in vacuo. The residue was purified by silica-gel chromatography, eluting with methylene chloride:5% ammonium hydroxide/methanol (97:3), to give 15.41 g of the title compound.

FDMS: m/z=242 (M+H).

Analysis calculated for $C_{12}H_{19}NO_4$: C, 59.74; H, 7.94; N, 5.81. Found: C, 59.78; H, 8.13; N, 5.77.

EXAMPLE 4

(−)-Diethyl 2-Aminobicyclo[3.1.0]hexane-2,6-dicarboxylate

A solution of the racemic mixture of compounds prepared as described in Example 3 (6.56 g) in ethyl acetate (100 mL) was treated with a solution of (+)-di-p-toluoyl-D-tartaric acid (12.0 g) in ethyl acetate (100 mL). After standing overnight at room temperature, the crystalline solid was removed by filtration and dried to give 14.7 g. Additional crystalline solid was obtained by cooling the filtrate to 0° C. The combined crystalline solids were dissolved in hot ethyl acetate, containing enough 2-propanol for complete dissolution. After cooling to 0° C., the crystalline solid was isolated by filtration, to give 2.3 g of a solid having an enantiomeric excess of ≧95%. The freebase form was obtained by partitioning the salt between aqueous sodium bicarbonate and ethyl acetate. The organic phase was separated, dried over potassium carbonate, filtered, and concentrated in vacuo to give 0.77 g of the title compound.

FDMS: m/z=242 (M+H).

Optical rotation: $\alpha_D$=−5.15° (c=1, EtOH).

Analysis calculated for $C_{12}H_{19}NO_4$: C, 59.74; H, 7.94; N, 5.81. Found: C, 59.68; H, 8.13; N, 5.58.

EXAMPLE 5

(+)-2-Aminobicyclo[3.1.0]hexane-2,6-dicarboxylic Acid

A solution of the compound prepared as described in Example 4 (0.69 g) in tetrahydrofuran (10 mL) was treated with 1N sodium hydroxide (10 mL), and the resulting mixture vigorously stirred at room temperature. After several days, the title compound was isolated by anion-exchange chromatography (Bio-Rad AG1-X8), eluting with 50% acetic acid/water, to give 0.53 g of the title compound.

FDMS: m/z=186 (M+H).

Optical rotation: $\alpha_D$=21.32° (c=1, 1N HCl).

Analysis calculated for $C_8H_{11}NO_4 \cdot 1.25H_2O$: C, 46.26; H, 6.55; N, 6.74. Found: C, 46.68; H, 6.47; N, 6.49.

EXAMPLE 6

2-Oxobicyclo[3.1.0]hexane-6-carboxylic acid

A mixture of 60 g of (1SR,5RS,6SR)ethyl 2-oxobicyclo [3.1.0]hexane-6-carboxylate and 300 ml of 1N sodium hydroxide was stirred at 25°–30° C. After 2.5 hours, concentrated hydrochloric acid was added to adjust the pH to 0.8–1.2. The resulting solution was extracted with ethyl acetate. The extracts were dried over magnesium sulfate, filtered, and concentrated to give 49.1 g (98%) of the crude material. Recrystallization from 100 ml of ethyl acetate gave the title compound, mp 123.5°–128° C.

FDMS: m/z=140 (M+)

Analysis calculated for $C_7H_8O_3$: C, 60.00; H, 5.75. Found: C, 60.14; H, 5.79.

EXAMPLE 7

2-Oxobicyclo[3.1.0]hexane-6-carboxylic acid salt with (S)-1-phenylethylamine

A solution of 14 g of the compound prepared in Example 6 in 140 ml of 25% ethanol in ethyl acetate was combined with (S)-1-phenylethylamine (1 eq.). After stirring overnight, the precipitated salt was isolated by filtration and dried to give 11.87 g (45.4%) of the desired salt. Conversion of the salt to the partially resolved 2-oxobicyclo[3.1.0] hexane-6-carboxylic acid by the method of Example 8 and analysis indicated that the salt was 68% ee. The enantiomeric excess was determined by conversion to the methyl ester with diazomethane followed by chiral HPLC on a Chiralpak AS column at 40° C. eluted with 10% isopropanol/90% hexane at 1 ml/min with detection at 210 nm.

EXAMPLE 8

(+)-2-Oxobicyclo[3.1.0]hexane-6-carboxylic acid

A mixture of 1.31 g of the product of Example 7 and 10 ml of 1N hydrochloric acid was stirred for 5 minutes and extracted with ethyl acetate. The extracts were dried over sodium sulfate, filtered, and concentrated to give 0.61 g of the title compound, mp 110°–115° C. The product was determined to be 68% ee by chiral HPLC (method of Example 7).

FDMS: m/z=141 (M+H)

Optical Rotation: $\alpha_D$=49.85°

EXAMPLE 9

(−)-2-Spiro-5'-hydantoinbicyclo[3.1.0]hexane-6-carboxylic acid

A solution of the compound prepared as described in Example 8 (68% ee, 1 eq.), potassium cyanide (1.25 eq.), and ammonium carbonate (2.5 eq) were combined and stirred in ethanol/water at 25° C. for 40 hours. The mixture was acidified with 6N hydrochloric acid, concentrated, diluted with water, and filtered to give a 79% yield of a 90:10 mixture of diastereomers, mp 286°–290° C. The diastereomeric mixture was recrystallized from isopropanol/water to give in 48% yield the title compound in 100% diastereomeric and 100% enantiomeric purity (enantiomeric ratio determined by chiral HPLC on a 4.6×150 mm Chiralcel OD-H column, eluted with 15% isopropanol/85% hexane at 1 ml/min at 40° C. with detection at 220 nm; diastereomeric ration determined by HPLC on a Zorbax SB-phenyl column at 40° C. with elution with 90:10 buffer/acetonitrile eluted at 2 ml/min with detection at 220 nm (buffer=0.1M dibasic sodium phosphate monohydrate adjusted to pH 2.1 with phosphoric acid).

FDMS: m/z=211 (M+H)

Optical Rotation: $\alpha_D=-25.98°$

Analysis calculated for C9H10N2O4: C, 51.43; H, 4.79; N, 13.33. Found: C, 51.38; H, 4.80; N, 13.26.

EXAMPLE 10

Ethyl 2-spiro-5'-hydantoinbicyclo[3.1.0]hexane-6-carboxylate

A mixture of 5.05 g of ethyl 2-oxobicyclo[3.1.0]hexane-6-carboxylate, 2.15 g of potassium cyanide, 5.77 g of ammonium carbonate, 30 ml of 2B-3 ethanol, and 12 ml of water was stirred at 35° C. until the reaction was complete by HPLC. After 15 hours, the reaction mixture was cooled to 0° C. and 33 ml of water was added to the mixture. After 2 hours at 0° C., the precipitate was isolated by filtration and dried to give 5.23 g (73%) of the title compound, mp 217°–220° C.

FDMS: m/z=238.1 (M+)

Analytical calculated for $C_{11}H_{14}N_2O_4$: C, 55.46; H, 5.92; N, 11.76. Found: C, 55.74; H, 5.88; N, 11.50.

EXAMPLE 11

2-Spiro-5'-hydantoinbicyclo[3.1.0]hexane-6-carboxylic acid

A mixture of 16.32 g of the product of Example 10 and 137 ml of 2N NaOH was stirred at 25° C. After 1 hour, concentrated hydrochloric acid was added to adjust the pH to 1.0. The resulting precipitate was isolated by filtration and dried to give 13.70 g (95%) of the title compound, mp 277°–279° C.

FDMS: m/z=210.1 (M+)

Analysis Calculated for $C_9H_{10}N_2O_4$: C, 51.43; H, 4.79; N, 13.33. Found: C, 51.70; H, 4.93; N, 13.43.

EXAMPLE 12

2-Spiro-5'-hydantoinbicyclo[3.1.0]hexane-6-carboxylic acid, (S)-1-phenylethylamine salt A mixture of 1.05 g of the product of Example 11 and 16.6 ml of a 1.6:1 solution of acetone:water was stirred at 25° C. while adding 1.53 g of R-(+)-1-phenylethylamine. The mixture was stirred for 2 hours at room temperature. The crystals were filtered, rinsed with acetone, and dried to give 0.74 g (45%) of the title compound, mp 205°–212° C.

Optical Rotation: $\alpha_D=-31.88°$ (c=1, methanol)

EXAMPLE 13

(−)-2-Spiro-5'-hydantoinbicyclo[3.1.0]hexane-6-carboxylic acid

A mixture of 0.74 g of the product of Example 12 and 10 ml of water was stirred at 25° C. while the pH was adjusted from 6.81 to 1.0 using 1N HCl. The reaction mixture was stirred for 1 hour and the product was collected by filtration and dried to give 0.35 g (75%) of the title compound, mp 310° C. (decomp).

FDMS: 210.1 (M+)

Optical Rotation: $\alpha_D=-24.22°$ (c=1, methanol)

Analysis calculated for $C_9H_{10}N_2O_4$: C, 51.43; H, 4.80; N,13.33. Found: C, 51.67; H, 4.87; N, 13.61.

EXAMPLE 14

(+)-2-Aminobicyclo[3.1.0]hexane-2,6-dicarboxylic Acid

A solution of 184 g of (−)-2-spiro-5'-hydantoinbicyclo [3.1.0]hexane-6-carboxylic acid and 1750 ml of 3N NaOH was heated at reflux until the reaction was complete by HPLC. After 28 hours, the solution was cooled to room temperature and filtered through glass paper to remove trace amounts of insoluble material. The pH of the solution was adjusted to 3.0 using concentrated HCl. The reaction mixture was stirred 1 hour at room temperature and two hours at 0° C. The precipitated product was collected by filtration, washed with 170 ml of cold water and dried to give 152.5 grams (86%) of the title compound.

FDMS: m/z=186.1 (m+1)

Optical rotation: $\alpha_D=23.18°$ (c=1, 1N HCl)

We claim:

1. A method of treating anxiety and related disorders in a mammal in need of treatment, which comprises administering an effective amount of an agonist which acts at negatively coupled cAMP-linked metabotropic glutamate receptors.

2. A method as claimed in claim 1, in which the agonist acts selectively at negatively coupled cAMP-linked metabotropic glutamate receptors.

3. A method of protecting a mammal from the effect of exposure to an anxiety-producing environment, which comprises administering an effective amount of an agonist which acts at negatively coupled cAMP-linked metabotropic glutamate receptors.

4. A method as claimed in claim 3, in which the agonist acts selectively at negatively coupled cAMP-linked metabotropic glutamate receptors.

5. A method as claimed in claim 2, in which the agonist is (+)-2-aminobicyclo[3.1.0]hexane-2,6-dicarboxylic acid.

6. A method as claimed in claim 4, in which the agonist is (+)-2-aminobicyclo[3.1.0]hexane-2,6-dicarboxylic acid.

* * * * *